United States Patent
Calogeropoulou et al.

(10) Patent No.: US 7,064,116 B2
(45) Date of Patent: Jun. 20, 2006

(54) GABA$_A$ MODULATING NEUROSTEROIDS

(76) Inventors: Theodora Calogeropoulou, 32 Proteos St., 14564 Kifissia (GR); Andrew Tsotinis, 20 Pontou St., 14572 Drosia (GR); Charikleia Souli, 128 Kononos St., 16231 Vironas (GR); Alexandros Makriyannis, 16 Stearns Rd., WaterTown, Boston, MA (US) 02472

( * ) Notice: Subject to any disclaimer, the term of this patent is extended or adjusted under 35 U.S.C. 154(b) by 309 days.

(21) Appl. No.: 10/250,334

(22) PCT Filed: Dec. 21, 2001

(86) PCT No.: PCT/GR01/00048

§ 371 (c)(1),
(2), (4) Date: Jun. 30, 2003

(87) PCT Pub. No.: WO02/053577

PCT Pub. Date: Jul. 11, 2002

(65) Prior Publication Data

US 2005/0176976 A1    Aug. 11, 2005

(30) Foreign Application Priority Data

Dec. 29, 2000    (GR) ................ 20000100470

(51) Int. Cl.
*A61K 31/56* (2006.01)
*C07J 7/00* (2006.01)
*C07J 9/00* (2006.01)
*C07J 41/00* (2006.01)

(52) U.S. Cl. .................... 514/177; 514/182; 552/9; 552/555; 552/599

(58) Field of Classification Search ............. 514/177, 514/182; 552/9, 555, 599
See application file for complete search history.

*Primary Examiner*—Barbara P. Badio
(74) *Attorney, Agent, or Firm*—Alix, Yale & Ristas, LLP

(57) ABSTRACT

The present invention relates to novel steroid derivatives that ace on the gamma-aminobutyric acid receptor-chloride ionophore (GR) complex as well as methods for making the same and their applications to induce anesthesia, in the treatment of stress, anxiety, PMS, PND, and seizures such as those caused by epilepsy, to ameliorate or prevent the attacks of anxiety, muscle tension, and depression common with patients suffering from central nervous system abnormalities. The present invention comprises a compound represented by Formula (I): wherein, R, $R_1$, $R_2$, $R_3$, $R_4$, $R_5$ are defined in the description of the invention. The present invention also includes formulations which consist of one or more of the compounds of Formula (I).

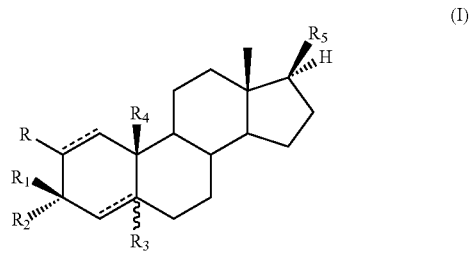

(I)

14 Claims, No Drawings

GABA$_A$ MODULATING NEUROSTEROIDS

The present application is the U.S. National Phase of PCT International Application No. PCT/GR01/00048 filed Dec. 21, 2001, which claims the benefit of Greek application No. 20000100470 filed on Dec. 29, 2000.

The present invention relates to novel steroid derivatives that act on the gamma-aminobutyric acid receptor-chloride ionophore (GR) complex as well as methods for making the same and their applications to induce anesthesia, in the treatment of stress, anxiety, PMS, PND, and seizures such as those caused by epilepsy, to ameliorate or prevent the attacks of anxiety, muscle tension, and depression common with patients suffering from central nervous system abnormalities.

BACKGROUND OF THE INVENTION

Neurosteroids are synthesized in the central and peripheral nervous system, particularly in myelinating glial cells, but also in astrocytes and many neurons and act in the nervous system (Paul, S. M., Purdy, R. H. Neuroactive steroids. *FASEB J.* 1992, 6, 2311–22; Robel, R., Baulieu, E. E. Neurosteroids biosynthesis and function. *Trends Endocrinol. Met* 1994, 5, 1–8; Kulkarni, S. K., Reddy, D. S. Neurosteroids: A new class of neuromodulators. *Drugs Today* 1995, 31, 433–55; Compagnone N. A., Mellon S. H. Neurosteroids: Biosynthesis and Function of These Novel Neuromodulators. *Frontiers in Neuroendocrinology* 2000, 21, 1–56). Research over the past decade has elucidated their multiple effects on various neurotransmitter systems (Majewska, M. D. Neurosteroids: Endogenous bimodal modulators of the GABA$_A$ receptor. Mechanism of action and physiological significance. *Prog. Neurobiol.* 1992, 38,379–95; Lambert, J. J, Belelli, D., Hill-Venning, C., Peters, J. A. Neurosteroids and the GABA$_A$ receptor function. *Trends Pharmacol. Sci.* 1995, 16, 95–303; Schumacher, M., Robel, P., Baulieu, E. E. Development and regeneration of the nervous system: A role for neurosteroids. *Dev. Neurosci.* 1996, 18, 16–21). The neuroactive steroids, allopregnanolone, allotetrahydrodeoxycorticosterone and progesterone act as allosteric agonists of the GABA$_A$ receptor and potentiate GABA$_A$ receptor Cl$^-$ channel responses (Majewska, M. D. Neurosteroids: Endogenous bimodal modulators of the GABA$_A$ receptor. Mechanism of action and physiological significance. *Prog. Neurobiol.* 1992, 38,379–95; Lan, N. C., Gee, K. W. Neuroactive steroid actions at the GABA$_A$ receptor. *Horm. Behav.* 1994, 28, 537–44; Goodnough, D. B., Hawkinson, J. E., Neuroactive steroid modulation of [$^3$H]muscimol binding to the GABA$_A$ receptor complex in rat cortex. *Eur. J. Pharmacol.* 1995, 288, 15762; Gee, K. W., McCauley, L. D., Lan, N. C., A putative receptor for neurosteroids on the GABA$_A$ receptor complex: The pharmacological properties and therapeutic potential of epalons. *Ctit. Rev. Neurobiol.* 1996, 9, 207–27). Pregnenolone sulfate and dehydroepiandrosterone sulfate however, have been shown to decrease GABA-mediated chloride currents (Mienville, J. M., Vicini, S., Pregnenolone sulfate antagonizes GABA$_A$ receptor-mediated currents via a reduction of chanel opening frequency. *Brain Res.* 1989, 489, 1904).

The GABA$_A$ receptor complex can exist as multiple isoforms and demonstrate a variety of pharmacological profiles that arise from their multimeric structure and the diversity of their component membranesubunits. The function of bezodiazepines requires a GABA$_A$ receptor complex comprised of α, β, and γ subunits, while t-butylbicycloorthobenzoate (TBPS, a noncompetitive antagonist at the receptor complex ), barbiturates, and neuroactive steroids will modulate the receptor complex comprised of only α and β subunits.

Recently, the existence of an additional novel modulatory site on gamma-amino butyric acid GABA$_A$ receptor complex for specific steroid metabolites, such as 5a-pregnan-3α-ol-20-one (5PG), a reduced progesterone metabolite, was demonstrated pharmacologically in brain homogenates and in expressed recombinant receptors. This steroid binding site is functionally coupled to other modulatory sites on the GABA$_A$ receptor complex (Lan, N. C., Chen, J-S., Johnson, D., Gee K. W. Differential effects of 4'-chlordiazepam on expressed human GABA$_A$ receptors. *J. of Neurochem.* 1995, 684–88). Electrophysiological studies performed on expressed GABA$_A$ receptors have shown modulatory and direct effects of steroids. According to Gee et al. (Gee K. W., Bolger, M. B., Wieland, S., Belleli, D., and Chen, J. S. Pharmacology of a GABA$_A$ receptor coupled steroid recognition site. *Synaptic Transmission* 1992, 111–17) and Wilson (Wilson, M. A., Influences of gender, gonadectomy, and estrous cycle on GABA/BZ receptors and benzodiazepine responses in rats. *Brain Res. Bull* 1992, 165–72) benzodiazepines and steroid hormone derivatives can potentiate the inhibitory actions of GABA through interactions with the GABA$_A$/BZ/chloride channel complex Binding of these steroid analogs to their respective site on the GABA$_A$/BZ/chloride channel complex causes a modification of all other receptor sites within the complex, including the benzodiazepine site. Therefore, neurosteroids allosterically enhance the binding of a benzodiazepine to the enzodiazepine receptor site.

The 3α-hydroxylated pregnane steroids have been shown to be potent anticonvulsants (Kokate T. G., Svensson, B. E., Rogawski M. A. Anticonvulsant activity of neurosteroids: Correlation with gamma-aminobutyric acid-evoked chloride current potentiation. *J. Pharmacol. Exp. Ther.* 1994, 279, 1223–1229; Frye C. A., The neurosteroid 3a,5a-THP has antiseizure and possible neuroprotective effects in an animal model of epilepsy. *Brain Res.* 1995, 696, 113–120), anxiolytics (Crawley J. N., Glowa J. R., Majewska M. D., Paul S. M. Anxiolytic activity of an endogenous adrenal steroid. *Brain Res.* 1986, 398, 382–5; Birtran D., Hilvers R. J., Kellogg C. K., Anxiolytic effects of 3α-hydroxy-5α[β]-pregnan-20-one: Endogenous metabolites of progesterone that are active at the GABA-A receptor. *Brain Res.* 1991, 561, 157–161; Birtran D., Shiekh M., McLeod M. *J. Neuroendocninol.* 1995, 7, 171–177) and antistress agents (Purdy R. H., Morrow A. L., Moore Jr P. H., Paul S. M. Stress-induced elevations of gamma-aminobutyric acid type-A active steroids in rat brain. *Proc. Natl. Acad. Sci. USA* 1991, 88, 45534557; Barbacia M. L., Roscetti G., Bolacchi F., Concas A., Mostallino M. C., Purdy, R. H., Biggio G. Stress-induced increase in brain neuroactive steroids: Antagonism by abecarnil. *Pharmacol. Biochem. Behav.* 1996, 54, 205–210) while, sulfated neurosteroids enhance memory performance in rodents (Floods J. F., Smith G. E., Roberts E. Dehydroepiandrosterone and its sulfate enhance memory retention in mice. *Brain Res.* 1988, 447, 269–278; Mayo W., Dellu F., Robel P., Cherkaoui J., Le Moal M., Baulieu E. E. Simon H. Infusion of neurosteroids into the nucleus basalis magnocellularis affects cognitive processes in the rat. *Brain Res.* 1993, 607, 324–328). The GABA$_A$ agonistic neurosteroids have been the subject of many publications (Han, M.; Hu, Y.; Zorumski, C. F.; Covey, D. F.; *J. Med. Chem*, 1995, 38, 4548–4556; Hu, Y.; Zorumski, C. F.; Covey, D. F.; *J. Med. Chem.*, 1993, 36, 3956–3967; Anderson, A.; Boyd, A. C.; Byford, A.; Campbell, A. C.; Gemmell, D. K; Hamilton, N. M.; Hill, D. R.; Hill-Venning, C.; Lambert, J. J.; Maidment, M. S.; May, V.; Marshall, R. J.; Peters, J. A.; Rees, D. C.; Stevenson, D.; Sundaram, H.; *J. Med. Chem.*, 1997, 40, 1668–1681; Hogenkamp, D. J.; Tahir, S. H.; Hawkinson, J. E.; Upasani, R. B.; Alauddin, M.; Kimbrough, C. L.; Acosta-Burruel, M.; Whittemore, E. R.; Woodward, R. M.; Lan, N. C.; Gee, K. W.; Bolger, M. B.; *J. Med. Chem.*, 1997, 40, 61–72; Upasani, R. B.; Yang, K. C.; Acosta-Burruel, M.; Konkoy, C. S.; McLellan, J. A.; Woodward, R. M.; Lan, N. C.; Carter, R. B.; Hawkinson, J. E.; *J. Med. Chem.*, 1997, 40, 73–84) and of several patents (U.S. Pat. No. 6,143,736, U.S. Pat. No. 5,939,545, U.S. Pat. No. 5,925,630, EP01038880, U.S. Pat. No. 5,591,733, WO 96116076, WO 95/21617, WO 94/27608, U.S. Pat. No. 5,232,917, WO 93/18053, WO 93/05786, WO 93/03732, US RE 035517, WO 91116897).

DETAILED DESCRIPTION OF THE INVENTION

1. A compound represented by Formula (I):

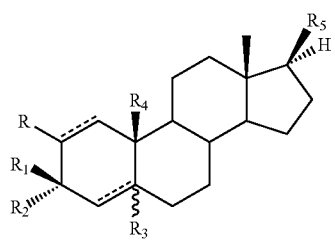

(I)

Wherein

R is one of hydrogen, amino, thio, sulfinyl, sulfonyl, sulfonamido, halogen, alkoxy, alkyl, alkenyl, alkynyl; all R groups can be optionally substituted.

$R_1$ is one of hydrogen, alkyl, alkenyl, arylkynyl, alkoxyalkyl, aminoalkyl, cyano, cyanoalkyl, thiocyanoalkyl, isothiocyano, azidoalkyl, arylalkyl, arylalkenyl, aryl, arylkylalkynyl, alkanoyloxyalkynyl, heteroaryloxyalkynyl, oxoalkynyl or a ketal thereof, cyanoalkynyl, heteroarylalkynyl, hydroxyalkynyl, alkoxyalkynyl, aminoalkynyl, acylaminoalkynyl, mercaptoalkynyl, hydroxyalkynyl dioic acid hemi-ester or a salt thereof, or alkynyloxyalkynyl; all $R_1$ groups can be optionally substituted.

$R_2$ is one of hydroxyl, alkoxy, alkanoyloxy, aminocarbonyloxy or alkoxycarbonyloxy; azido, NCS;

$R_3$ is hydrogen, or when a double bond is present between C4 and C5 of the steroid ring system, then $R_3$ is not present;

$R_4$ is one of hydrogen or lower alkyl, $R_5$ is one of —CH(OR$_6$)R$_7$, —C≡C-aryl, —C≡C—CH(OR$_6$)R$_8$, —C≡C—C(O)R$_8$ $R_5$ is one of —CH(X)—R$_6$ $R_5$ is one of —C(O)CH$_2$N$_3$, —C(O)CH$_2$Br, —C(O)CH$_3$ $R_6$ is independently H, optionally substituted $C_{1-10}$alkyl, optionally substituted $C_{2-10}$alkenyl, optionally substituted $C_{2-10}$alkynyl, optionally substituted aryl, optionally substituted arylkyl, optionally substituted C(O)—$C_{1-10}$alkyl, optionally substituted C(O)—$C_{2-10}$alkenyl, optionally substituted C(O)—$C_{2-10}$alkynyl $R_7$ is independently allene, optionally substituted alkynyl, optionally substituted arylkylalkynyl, optionally substituted alkanoyloxyalkynyl, optionally substituted heteroaryloxyalkynyl, oxoalkynyl or a ketal thereof, cyanoalkynyl, hydroxyalkynyl, alkoxyalkynyl, aminoalkynyl, acylaminoalkynyl, mercaptoalkynyl, hydroxyalkynyl dioic acid hemi-ester or a salt thereof, or alkynyloxyalkynyl;

$R_8$ is independently H, $C_{1-10}$alkyl, $C_{2-10}$alkenyl, $C_{2-10}$alkynyl, arylalkyl, aryl, all of which may be optionally substituted X is one of $N_3$, CN, NCS and the dotted lines indicate that a single or double bond may be present; provided that:

when $R_5$ is one of —CH(X)—$R_6$, then $R_1$ is other than hydrogen; or when $R_5$ is one of —C(O)CH$_2$N$_3$, —C(O)CH$_2$Br, —C(O)CH$_3$, then $R_2$ is $N_3$ As provided herein, the following terms alone or in combination, are defined herein as follows:

The term "alkyl" is defined herein to be straight chain or branched chain or cyclic saturated hydrocarbon groups which may be optionally substituted. Preferable are $C_2$ to $C_{16}$ alkyl groups.

The term "haloalkyl" is defined herein as an alkyl substituted with one or more halogens.

The term "alkenyl" alone or in combination, is defined herein to be straight chain or branched chain or cyclic unsaturated hydrocarbon groups which contain at least one carbon-carbon double bond and all of which may be optionally substituted. Preferable are $C_2$ to $C_{16}$ alkenyl groups.

The term "alkynyl" alone or in combination, is defined herein to be straight chain or branched chain hydrocarbon groups which contain at least one carbon-carbon triple bond and all of which may be optionally substituted. Preferable are $C_2$ to $C_{16}$ alkynyl groups The term "aryl" alone or in combination, is defined herein to be aromatic groups which contain at least one ring with conjugated π electrons carboxylic aryl groups, and diaryl groups which may be optionally substituted. Preferable are $C_2$ to $C_{10}$ aryl groups.

The term "thio" refers to —SR$_9$, where R$_9$ is hydrogen, alkyl, alkenyl, alkynyl, aryl or arylalkyl.

The term "sulfinyl" refers to —SOR$_{10}$, where R$_{10}$ is hydrogen, alkyl, alkenyl, alkynyl, aryl or arylalkyl.

The term "sulfonyl" refers to —SO$_2$R$_{11}$, where R$_{11}$ is hydrogen, alkyl, alkenyl, alkynyl, aryl or arylalkyl.

The term "sulfonamido" refers to —SO$_2$NR$_{12}$R$_{13}$, wherein R$_{12}$ and R$_{13}$ are independently hydrogen or lower alkyl.

The term "optionally substituted" or "substituted," refers to groups substituted by one to five substituents, independently selected from lower alkyl (acyclic and cyclic), aryl (carboaryl and heteroaryl), alkenyl, alkynyl, alkoxy, halo, haloalkyl, amino, mercapto, alkylthio, alkylsulfinyl, alkylsulfonyl, nitro, alkanoyl, alkanoyloxy, alkanoyloxyalkanoyl, alkoxycarboxy, carbalkoxy, carboxamido, formyl, carboxy, hydroxy, cyano, azido, keto and cyclic ketals thereof, alkanoylamido, heteroaryloxy.

The term "lower" is referred to herein in connection with organic radicals or compounds defines one up to and including six carbon atoms. Such groups may be straight chain, branched chain, or cyclic.

The term "heteroaryl" refers to carbon containing 5–14 membered cyclic unsaturated radicals containing one, two, three or four O, N or S atoms and having 6, 10 or 14π electrons delocalized in one or more rings, e.g., pyridine, oxazole, indole, purine, pyrimidine, imidazole, benzimidazole, each of which may be optionally substituted as discussed above.

The present invention also includes pharmaceutically acceptable esters and salts of the compounds of Formula (I), including acid addition salts.

Those skilled in the art will recognize that stereocenters exist in compounds of Formula (I). Accordingly, the present invention includes all possible stereoisomers and geometric isomers of Formula (I) as a mixture or as pure diastereomers. When a compound of Formula (I) is desired as a single diastereomer, it may be obtained either by resolution of the final product or by stereospecific synthesis from either isomerically pure starting material or any convenient intermediate.

The compounds of the present invention possess agonistic activity for the $GABA_A$ receptor. Desirable objects of the pharmaceutical compositions and methods of this invention are to induce anesthesia, the treatment of stress, anxiety, PMS, PND, and seizures such as those caused by epilepsy to ameliorate or prevent the attacks of anxiety, muscle tension, and depression common with patients suffering from central nervous system abnormalities.

Formulations of the present invention may be administered in standard manner for the treatment of the indicated diseases, such as orally, parenterally, sublingually, transdermally, rectally via inhalation or via buccal administration. Additionally, compositions of the present invention may be formulated for parenteral administration by injection or continuous infusion. The composition according to the invention may be formulated as a slow release form or as a depot preparation.

Some specific compounds of Formula (I) are listed below, the synthesis of which was performed in accordance with the Example section set forth below.

17β-[2-(4-tolyl)ethynyl]-5α-androstane-3α-ol
17β-(2-methoxycarbonylethynyl)-5α-androstane-3α-ol
17β-(2-bromoethynyl)-5α-androstane-3α-ol
17β-(3-hydroxy-1-butynyl)-5α-androstane-3α-ol
17β-(3-oxo-1-butynyl)-5α-androstan-3α-ol
17β-[1-hydroxy-3-(4-methoxyphenyl)-2-propynyl]-5α-androstan-3α-ol
17β-(1-hydroxy-2,3-butadienyl)-5α-androstane-3-ol
17β-(1-methoxy-2-propynyl)-5α-androstan-3a-ol
17β-(1-hydroxy-2-propynyl)-5α-androstan-3-ol
3α-Azido-5α-pregnan-20-one
3α-Azido-21-bromo-5α-pregnan-20-one
3α,21-di-azido-5α-pregnan-20-one

EXPERIMENTAL SECTION

NMR spectra were recorded on a Bruker AC 300 spectrometer operating at 300 MHz for $^1H$ and 75.43 MHz for $^{13}C$. $^1H$ NMR spectra are reported in units of δ relative to internal $CHCl_3$ at 7.24 ppm. $^{13}C$ NMR shifts are expressed in units of δ relative to $CDCl_3$ at 77.0 ppm. $^{13}C$ NMR spectra were proton noise decoupled. All NMR spectra were recorded in $CDCl_3$. Silica gel plates (Merck F254) were used for thin layer chromatography. Chromatographic purification was performed with silica gel (200–400 mesh).

Example 1

1,1-Dibromo-2-[3α-(t-butyidiphenyisilyloxy)-5α-androstan-17β-yl]-ethylene

To a solution of tetrabromomethane (1.99 g, 6 mmol) in anhydrous methylene chloride (31 mL) was added at 0° C., triphenylphosphine (3.14 g, 6 mmol) and the resulting mixture is stirred for 10 min. Subsequently, a solution of 3α-(t-butyidiphenylsilyloxy)-5α-androstan-17β-carboxaldehyde (540 mg, 1 mmol) in methylene chloride (6 mL) was added and the mixture was stirred at 0° C. for an additional 10 min. The reaction mixture was diluted with ethyl acetate and the organic layer is washed with water, saturated aqueous NaCl solution and was dried with anhydrous $Na_2SO_4$. The solvent was evaporated in vacuo and the residue was purified with flash column chromatography using petroleum ether/ether 95/5 as eluent afforded the desired compound named.

Yield: 560 mg, 93% m.p.: 69–71° C.

$^1H$ NMR δ: 0.66 (s, 3H, 18-$CH_3$), 0.71 (s, 3H, 19-$CH_3$), 0.81–1.72 (m, 22H), 1.05 (s, 9H, $C(CH_3)_3$), 2.32–2.35 (m, 1H, 17a-H), 3.99 (bs, 1H, 3β-H), 6.28–6.31 (d, J=9.5 Hz, 1H, 20-H), 7.34–7.39 (m, 6H, aromatic), 7.62–7.64 (m, 4H, aromatic).

$^{13}C$ NMR δ: 11.48, 13.56, 14.20, 19.36, 20.39, 21.06, 24.92, 27.05, 28.51, 29.32, 32.29, 32.71, 35.59, 36.08, 37.96, 39.31, 45.52, 54.49, 55.29, 60.40, 68.03, 87.59, 127.43, 129.39, 134.76, 135.84, 140.89.

Elemental analysis $C_{37}H_{50}OSiBr_2$% Theor. C:63.61, H:7.21, Found. C:63.42, H:7.19.

Example 2

17β-(2-bromoethynyl)-5α-androstane-3α-ol

A solution of 1,1-dibromo-2-[3α-(t-butyldiphenylsilyloxy)-5α-androstan-17β-yl]-ethylene (0.074 mmol) in anhydrous tetrahydrofuran (3 mL) was treated with a 1M solution of $(n-Bu)_4N^+F^-$ (1.48 mL, 1.48 mmol) and the resulting solution was stirred at RT for 48 h. The mixture was quenched with saturated aqueous $NH_4Cl$ solution. Ethyl acetate was added and the organic layer was extracted with water and brine and was dried ($Na_2SO_4$). Evaporation of the solvent in vacuo followed by purification of the residue with flash column chromatography using methylene chloride/ethyl acetate 95/5 as eluent afforded the desired compound named above.

Yield: 70% m.p.: 165–167° C.

$^1H$ NMR δ: 0.75 (s, 3H, 18-$CH_3$), 0.76 (s, 3H, 19-$CH_3$), 0.89–1.79 (m, 22H), 2.15 (t, J=9.5 Hz, 1H, 17α-H), 4.01 (bs, 1H, 3β-H).

$^{13}C$ NMR δ: 11.18, 13.74, 20.52, 24.52, 28.45, 28.73, 29.02, 32.01, 32.19, 35.84, 36.03, 36.17, 37.37, 39.02, 39.14, 43.22, 44.32, 54.34, 54.60, 66.52, 81.89. Elemental analysis:$C_{21}H_{31}OBr$ % Υπολ. C:66.49, H:8.24, Found C:66.23, H:8.08.

Example 3

17β-ethynyl-3α-(t-butyldiph nylsilyloxy)-5α-androstan

To a solution of 1,1-dibromo-2-[3α-(t-butyldiphenylsilyloxy)-5α-androstan-17β-yl]-ethylene (230 mg, 0.33 mmol) in anhydrous tetrahydrofuran (8 mL) was added at −78° C. a solution of n-BuLi 1.6 M in hexanes (0.45 mL, 0.72 mmol) and the resulting mixture was stirred at −78° C. for 1 hour. The mixture was quenched by the addition of saturated aqueous $NH_4Cl$ solution. Ethyl acetate was added and the organic layer was extracted with water and brine and was dried ($Na_2SO_4$). Evaporation of the solvent in vacuo followed by purification of the residue with flash column chromatography using petroleum ether/ether 97/3 as eluent afforded the desired compound named above.

Yield: 160 mg, 89%
m.p.: 60–62° C.
$^1$H NMR δ: 0.71 (s, 3H, 19-CH$_3$), 0.76 (s, 3H, 18-CH$_3$), 1.04 (s, 9H, C(CH$_3$)$_3$), 1.21–2.02 (m, 23H), 2.06 (d, J=2.31 Hz, 1H), 3.99 (bs, 1H, 3β-H), 7.33–7.35 (m, 6H), 7.62–7.64 (m, 4H).
$^{13}$C NMR δ: 11.43, 13.57, 14.11, 19.35, 20.61, 24.59, 27.05, 28.49, 29.14, 29.32, 29.69, 32.27, 32.71, 36.11, 37.34, 39.39, 42.01, 43.96, 54.59, 54.78, 68.63, 69.74, 86.22, 127.42, 129.37, 134.87, 135.76.
Elemental analysis:C$_{37}$H$_{50}$OSi % Calc. C:82.47, H:9.35, Found. C:82.07, H:9.69.

Example 4

3α-(t-butyldiphenylsilyloxy)-17β-[2-(4-tolyl)ethynyl]-5α-androstane

A solution of 17β-ethynyl-3α-(t-butyidiphenylsilyloxy)-5α-androstane (120 mg, 0.23 mmol) in pyrrolidine (2 mL) was added to a mixture of tetrakis triphenylposphine palladium (0) (13.28 mg, 0.0115 mmol) and CuI (4.4 mg, 0.023 mmol) in pyrrolidine (1 mL). To the resulting mixture was added 4-iodotoluene (150 mg, 0.69 mmol) and was stirred at RT for 24 h. Addition of saturated aqueous NH$_4$Cl solution followed by ethyl acetate. Extraction of the organic layer with water and brine and drying (Na$_2$SO$_4$) followed by evaporation of the solvent in vacuo and subsequent purification of the residue with flash column chromatography using petroleum ether/acetone 80/20 as eluent afforded the desired compound named above.

Yield: 100 mg, 72%
m.p.: 791° C.
$^1$H NMR δ: 0.73 (s, 3H, 19-CH$_3$), 0.83 (s, 3H, 18-CH$_3$), 1.07(s, 9H, C(CH$_3$)$_3$), 1.12–2.25 (m, 23H), 2.32 (s, 3H), 4.01 (bs, 1H, 3β-H), 7.06 (d, J=7.9 Hz, 2H), 7.31 (d, J=7.9 Hz, 2H), 7.35–7.43 (m, 6H), 7.63–7.66 (m, 4H).
$^{13}$C NMR δ: 11.45, 13.82, 19.35, 20.67, 21.38, 24.68, 27.06, 28.53, 29.34, 32.32, 32.74, 36.13, 36.20, 37.47, 37.55, 39.42, 42.96, 44.53, 48.91, 54.65, 51.86, 68.06, 82.43, 91.07, 121.22, 127.43, 128.85, 129.38, 131.44, 134.79, 135.77, 137.24.
Elemental analysis: C$_{44}$H$_{56}$OSi % Calc C:84.02, H:8.98, Found C:83.89, H:8.67.

Example 5

17β-[2-(4-tolyl)ethynyl]-5α-androstane-3α-ol

A solution of 3α-(t-butyldiphenylsilyloxy)-17β-[2-(4-tolyl)ethynyl]-5α-androstane (80 mg, 0.13 mmol) in anhydrous tetrahydrofuran (5.2 mL) was treated with a 1M solution of (n-Bu)$_4$N$^+$F$^-$ (2.6 mL, 2.6 mmol) and the resulting solution was stirred at RT for 48 h. Work up of the reaction was accomplished as in Example 2. Purification by flash column chromatography using dichloromethane as eluent afforded the desired product named above.

Yield: 25 mg, 50%
m.p.: 178–180° C.
$^1$H NMR δ: 0.77 (s, 3H, 19-CH$_3$), 0.81 (s, 3H, 18-CH$_3$), 0.86–2.08 (m, 23H), 2.30 (s, 3H), 4.02 (bs, 1H, 3β-H), 7.03–7.06 (d, J=7.97 Hz, 2H), 7.25–7.27 (d, J=7.97 Hz, 2H).
$^{13}$C NMR δ: 11.18, 13.77, 20.57, 21.31, 24.61, 28.74, 28.99, 29.28, 32.05, 32.19, 35.84, 36.11, 36.16, 37.48, 39.14, 42.88, 44.44, 54.40, 54.83, 66.51, 82.43, 90.94, 121.18, 128.81, 131.38, 137.17.
Elemental analysis C$_{28}$H$_{38}$O % Calc C:86.09, H:9.81, Found C:85.73, H:9.60.

Example 6

3-[3α-(t-butyidiphenylsilyloxy-5α-androstane-17β-yl]methylpropynoate

To a solution of 1,1-dibromo-2-[3α-(t-butyidiphenylsilyloxy)-5α-androstan-17β-yl]-ethylene in tetrahydrofuran (1.75 mL) was added at –78° C. a solution of n-BuLi (0.096 mL, 0.154 mmol), 1.6 M in hexanes and the resulting mixture was stirred for 1 h. Subsequently methylchloroformate (0.3 mL, 3.88 mmol) was added at –78° C. and the mixture was let warm up to RT over 3 h. The reaction mixture was quenched with saturated aqueous NH$_4$Cl solution followed by ethyl acetate. Extraction of the organic layer with water and brine and drying (Na$_2$SO$_4$) followed by evaporation of the solvent in vacuo and subsequent purification of the residue with flash column chromatography using petroleum ether/ether 97/3 as efuent afforded the desired compound named above.

Yield: 26 mg, 61%
m.p.: 75–77° C.
$^1$H NMR δ: 0.70 (s, 3H, 19-CH$_3$), 0.80 (s, 3H, 18-CH$_3$), 1.04 (s, 9H, C(CH$_3$)$_3$), 0.83–2.26 (m, 22H), 2.30 (m, 1H, 17α-H), 3.73 (s, 3H, CO$_2$CH$_3$) 3.99 (bs, 1H, 3β-H), 7.30–7.38 (m, 6H), 7.62–7.64 (m, 4H).
$^{13}$C NMR δ: 11.44, 13.91, 14.12, 16.29, 19.37, 20.59, 24.69, 27.07, 28.50, 29.32, 29.70, 32.26, 32.72, 36.10, 37.42, 39.39, 41.95, 45.01, 52.49, 54.51, 55.06, 68.03, 74.68, 91.63, 127.44, 129.40, 134.78, 135.77, 154.47.
Elemental analysis C$_{39}$H$_{52}$O$_3$Si % Calc. C:78.47, H:8.78, Found C:78.06, H:9.14.

Example 7

17β-(2-methoxycarbonylethynyl)-5α-androstane-3α-ol

A solution of 3-[3α-(t-butyidiphenylsilyloxy-5α-androstane-17β-yl]methylpropynoate (24 mg, 0.04 mmol) in anhydrous dichloromethane (2.5 mL) was treated with HF pyridine (0.24 mmol, 0.007 mL) at 0° C. and the resulting mixture was stirred at RT for 2 h. Addition of water at 0° C. was followed by extraction with methylene chloride. The organic layer was washed with brine and was dried with (Na$_2$SO$_4$) and the solvent was evaporated in vacuo. Subsequent purification of the residue with flash column chromatography using dichloromethane/ethyl acetate 95/5 as eluent afforded the desired compound named above.

Yield: 9.31 mg, 65%
m.p.: 135–137° C.
$^1$H NMR δ: 0.76 (s, 3H, 19-CH$_3$), 0.79 (s, 3H, 18-CH$_3$), 0.83–2.06 (m, 22H), 2.28 (t, J=8.38 Hz, 1H, 17α-H), 3.73 (s, 3H, CO$_2$CH$_3$), 4.02 (bs, 1H, 3β-H).
$^{13}$C NMR δ: 11.19, 13.90, 20.48, 24.65, 28.45, 29.06, 32.00, 32.16, 35.79, 35.97, 36.15, 37.34, 39.08, 41.84, 44.93, 52.53, 54.20, 54.99, 66.49, 74.64, 84.82, 91.55, 154.46.
Elemental analysis C$_{23}$H$_{34}$O$_3$% Calc C:77.05, H:9.56, Found. C:76.70, H:9.88.

Example 8

4[3α-(t-butyldiphenylsilyloxy)-5α-androstan-17β-yl]-3-butyn-2-ol

To a solution of 1,1-dibromo-2-[3α-(t-butyidiphenylsilyloxy)-5α-androstan-17β-yl]-ethylene (308 mg, 0.44 mmol) in THF (11 mL) was added at –78° C. a solution of n-BuLi 1.6 M in hexanes (2.76 mL, 4.4 mmol) and the mixture was stirred for 2 h. Acetaldehyde (0.032 mL, 0.57 mmol) was added at −78° C. and the temperature was let to rise to 25° C. Addition of HCl solution 2N at 0° C. was followed by extraction with ethyl acetate. The organic layer was washed with NaHCO$_3$ brine and dried with (Na$_2$SO$_4$) and the solvent was evaporated in vacuo. Subsequent purification of the residue with flash column chromatography using petroleum etherlethyl acetate 90/10 as eluent afforded the desired compound named above.

Yield: 160 mg, 62% m.p.: 68–70° C.

$^1$H NMR δ: 0.71 (s, 3H, 19-CH$_3$), 0.73 (s, 3H, 18-CH$_3$), 1.06 (s, 9H, C(CH$_3$)$_3$), 0.79–2.03 (m, 22H), 1.42 (s, 3H, CH(OH)CH$_3$), 2.18 (t, J=9.2 Hz, 1H, 17α-H), 4.01 (bs, 1H, 3β-H), 4.54 (bs, 1H, CH(OH)CH$_3$), 7.32–7.42 (m, 6H), 7.64–7.65 (m, 4H).

$^{13}$C NMR δ: 11.43, 13.68, 14.18, 19.35, 20.61, 24.57, 24.97, 27.05, 28.49, 29.19, 29.32, 32.27, 32.71, 36.12, 37.41, 39.40, 42.15, 44.08, 54.60, 54.77, 58.71, 60.39, 68.03, 84.20, 86.05, 127.42, 129.37, 134.77, 135.76.

Elemental analysis C$_{39}$H$_{54}$O$_2$Si % Calc. C:80.36, H:9.34, Eup. C:79.98, H:9.46.

Example 9

17β-(3-hydroxy-1-butynyl)-5α-androstane-3α-ol

A solution of 4[3α-(t-butyidiphenylsilyloxy)-5α-androstan-17β-yl]-3-butyn-2-ol (30 mg, 0.052 mmol) in anhydrous tetrahydrofuran (2 mL) was treated with a 1M solution of (n-Bu)$_4$N$^+$F$^-$ (1.04 mL, 1.04 mmol) and the resulting solution was stirred at RT for 24 h. Addition of saturated aqueous NH$_4$Cl solution was followed by extraction with ethyl acetate. The organic layer was extracted with water, brine and was dried with Na$_2$SO$_4$, and the solvent was evaporated in vacuo. Subsequent purification of the residue with flash column chromatography using methylene chloride/ethyl acetate 90/10 as eluent afforded the desired compound named above.

Yield: 14.7 mg, 83% m.p.: 169–171° C.

$^1$H NMR δ: 0.72 (s, 3H, 18-CH$_3$), 0.76 (s, 3H, 19-CH$_3$), 0.83–1.99 (m, 22H), 1.39 (s, 3H, CH(OH)CH$_3$), 2.14 (t, J=9.36 Hz, 1H, 17α-H), 4.01 (bs, 1H, 3β-H), 4.5 (m, 1H. CH(OH)CH$_3$).

$^{13}$C NMR (CDCl$_3$) δ: 11.19, 13.68, 20.53, 24.53, 24.95, 28.46, 29.01, 29.15, 32.04, 32.20, 35.84, 36.06, 36.17, 37.38, 39.15, 42.10, 44.02, 54.38, 54.77, 58.68, 66.52, 84.22, 85.94.

Elemental analysis C$_{23}$H$_{36}$O$_2$% Calc. C:80.18, H:10.53, Found. C:79.83, H:10.77.

Example 10

4[3α-(t-butyldiphenylsilyloxy)-5α-androstan-17β-yl]-3-butyn-2-one

Pyridinium chlorochromate (22 mg, 0.10 mmol) was added to anhydrous methylene chloride (1 mL) and to the resulting mixture was added a solution of 4[3α-(t-butyldiphenylsilyloxy)-5α-androstan-17β-yl]-3-butyn-2-ol (30 mg, 0.053 mmol) in dichloromethane (2.5 mL) and the resulting mixture was stirred for 3 h at RT. Subsequently the mixture was fitered through florisil, washed with ether and the solvent was removed in vavuo. Purification of the residue using flash column chromatography, petroleum ether/ethyl acetate 97/3 elution solvent, afforded the product mentioned above.

Yield: 20 mg, 67% m.p.: 63–66° C.

$^1$H NMR δ: 0.72 (s, 3H, 19-CH$_3$), 0.80 (s, 3H, 18-CH$_3$), 1.10 (s, 9H, C(CH$_3$)$_3$), 1.12–2.19 (m, 23H), 2.32 (s, 3H, COCH$_3$), 4.01 (bs, 1H, 3β-H), 7.32–7.40 (m, 6H), 7.63–7.66 (m, 4H).

$^{13}$C NMR δ: 11.42, 13.94, 19.35, 20.59, 24.69, 27.06, 28.44, 28.66, 29.31, 29.90, 32.25, 32.71, 32.91, 36.10, 37.45, 39.38, 42.23, 45.01, 54.51, 55.07, 68.01, 77.25, 83.33, 96.02, 127.42, 129.39, 134.76, 135.75, 184.97.

Elemental analysis C$_{39}$H$_{52}$O$_2$Si % Calc C:80.63, H:9.02, Found. C:80.25, H:8.98.

Example 11

17β-(3-oxo-1-butynyl)-5α-androstan-3α-ol

A solution of 4[3α-(t-butyidiphenylsilyloxy)-5α-androstan-17β-yl]-3-butyn-2-one (40 mg, 0.07 mmol) in anhydrous dichloromethane (2.8 mL) was treated with HF pyridine (0.008 mL, 0.28 mmol) at 0° C. and the resulting mixture was stirred at RT for 2 h. Addition of water at 0° C. was followed by extraction with methylene chloride. The organic layer was washed with brine and was dried with Na$_2$SO$_4$ and the solvent was evaporated in vacuo. Subsequent purification of the residue with flash column chromatography using dichloromethane/ethyl acetate 95/5 as eluent afforded the desired compound named above.

Yield: 18 mg, 76% m.p.: 148–150° C.

$^1$H NMR δ: 0.77 (s, 3H, 19-CH$_3$), 0.78 (s, 3H, 18-CH$_3$), 0.85–2.27 (m, 23H), 2.30 (s, 3H, COCH$_3$), 4.02 (bs, 1H, 3β-H).

$^{13}$C NMR δ: 11.17, 13.92, 20.51, 24.65, 28.41, 28.62, 29.01, 32.01, 32.19, 32.90, 35.82, 36.02, 36.16, 37.41, 39.11, 42.16, 44.94, 54.25, 55.06, 66.46, 83.31, 95.93, 184.96. IR(cm$^{-1}$): 2202 (C≡C), 1669 (C=O)

Elemental analysis C$_{23}$H$_{34}$O$_2$% Calc. C:80.64, H:10.01, Found. C:80.38, H:9.76.

Example 12

3-Trimethylsilyl-1-[3α(t-butyidiphenylsilyloxy)-5α-androstan-17β-yl]-2-propyn-1-ol To a solution of trimethylsilylacetylene (0.24 mL, 1.715 mmol) in anhydrous THF (5.7 mL) at 0° C. was added a solution of n-BuLi (1.07 mL, 1.715 mmol) 1.6 M in hexanes and the resulting mixture was stirred for 2 h. Subsequently, the mixture was cooled to −78° C. and a solution of 3α-(t-butyidiphenylsilyloxy)-5α-androstan-17β-carboxaldehyde (310 mg, 0.57 mmol) in THF (5.7 mL) was added and the mixture was stirred at this temperature for 3 h. Quenching of the reaction by the addition of NH$_4$Cl was followed by extraction with ethyl acetate.

The organic layer was washed with water, brine, dried with (Na$_2$SO$_4$) and the solvent was evaporated in vacuo. Subsequent purification of the residue with flash column chromatography using petroleum etherlacetone 92/8 as eluent afforded the two diastereomers of the desired compound named above.

Yield: (85% totally)

Less polar diastereomer (233 mg)

m.p.: 68–71° C.

¹H NMR δ: 0.15 (s, 9H, Si(CH₃)₃), 0.71 (s, 6H, 18,19-CH₃), 0.84–2.07 (m, 23H), 1.06 (s, 9H, C(CH₃)₃), 3.99 (bs, 1H, 3β-H), 4.27 (d, J=9.54 Hz, 1H, 20-H), 7.32–7.42 (m, 6H, aromatic), 7.63–7.66 (m, 4H, aromatic).

¹³C NMR δ: 0.09, 11.39, 12.39, 19.36, 20.62, 24.30, 25.42, 27.06, 28.55, 29.32, 32.23, 32.66, 35.47, 36.05, 36.17, 39.36, 39.56, 42.54, 54.56, 56.00, 56.75, 65.21, 68.08, 91.48, 107.43, 127.42, 129.37, 134.90, 135.77.

Elemental analysis $C_{41}H_{59}O_2Si_2$% Calc C:76.95, H:9.30, Found C:76.54, H:9.2.

More polar diastereomer (78 mg)
m.p.: 62–65° C.

¹H NMR δ: 0.15 (s, 9H, Si(CH₃)₃), 0.68 (s, 3H, 18-CH₃), 0.71 (s, 3H, 19-CH₃), 0.75–2.23 (m, 23H), 1.05 (s, 9H, C(CH₃)₃), 3.99 (bs, 1H, 3βH), 4.10–4.15 (m, 1H, 20-H), 7.31–7.39 (m, 6H, aromatic), 7.62–7.65 (m, 4H, aromatic).

¹³C NMR δ: 0.17, 11.49, 12.78, 19.39, 20.51, 23.91, 26.62, 27.08, 28.58, 29.37, 32.30, 32.75, 35.25, 36.08, 36.21, 38.61, 39.42, 41.92, 54.62, 56.20, 56.72, 64.92, 68.11, 90.23, 107.31, 127.46, 129.40, 134.83, 135.80.

Elemental analysis $C_{41}H_{59}O_2Si_2$% Calc. C:76.95, H:9.30, Found. C:76.73, H:9.08.

Example 13

17β-(1-hydroxy-2-propynyl)-5α-androstan-3-ol

A solution of each diastereomer of Example 12 (200 mg, 0.31 mmol) in THF (6.5 mL) was treated with a solution of (n-Bu)₄N⁺F⁻ (7.8 mL, 7.8 mmol) 1M in THF at RT for 24 h. The reaction was worked up as in Example 7 to afford after purification by flash column chromatography using dichloromethane/ethyl acetate 90/10 as elution solvent the compound named above.

Yield: 83 mg, 80.5%
Less polar diastereomer
m.p.: 197–199° C.

¹H NMR δ: 0.73 (s, 3H, 18-CH₃), 0.77 (s, 3H, 19-CH₃), 0.80–2.10 (m, 23H), 2.41 (d, J=1.81 Hz, 1H), 4.03 (bs, ₁H, 3β-H), 4.24–4.72 (m, 1H, 20-H).

¹³C NMR δ: 11.23, 12.24, 20.59, 24.30, 25.34, 28.53, 29.03, 32.03, 32.20, 35.43, 35.91, 36.15, 39.16, 39.63, 42.56, 54.45, 56.07, 56.67, 64.68, 66.01, 72.50, 85.44. Elemental analysis $C_{22}H_{34}O_2$% Calc. C:79.95, H:10.37, Found. C:79.56, H: 10.48.

More polar diastereomer
m.p.: 187–190° C.

¹H NMR δ: 0.69 (s, 3H, 18-CH₃), 0.77 (s, 3H, 19-CH₃), 0.79–2.21 (m, 23H), 2.49 (d, J=2.02 Hz, 1H), 4.03 (bs, 1H, 3β-H), 4.15 (d, J=8.6 Hz, 1H, 20-H).

¹³C NMR δ: 11.17, 12.73, 20.40, 23.84, 26.32, 28.51, 29.02, 32.02, 32.16, 35.13, 35.87, 36.11, 38.51, 39.15, 41.87, 54.38, 56.19, 56.48, 64.15, 66.58, 85.28. Elemental analysis $C_{22}H_{34}O_2$% Calc C:79.95, H:10.37, Found C:79.60, H:10.51.

Example 14

17β-(1-hydroxy-2,3-butadienyl)-5α-androstane-3-ol

To a solution of each of the two diastereomers of Example 13 (83 mg, 0.25 mmol) in anhydrous dioxane (3 mL) were sequentially added paraformaldehyde (20 mg), copper hypobromide (4 mg, 0.027 mmol) and diisopropylamine (0.07 mL, 0.5 mmol). The resulting mixture was refluxed for 24 h. Addition of HCl 2N and extraction with ethyl acetate was followed by extraction of the organic layer with NaHCO₃, water and brine and drying with Na₂SO₄. The solvent was evaporated in vacuo and the residue was purified by flash column chromatography using dichloromethane/ethyl acetate 85/15 as elution solvent to afford the compound named above.

Yield: 45 mg, 52%
Less polar diastereomer
m.p.: 184–187° C.

¹H NMR δ: 0.76 (s, 3H, 18-CH₃), 0.78 (s, 3H, 19-CH₃), 0.85–2.10 (m, 23H), 4.03 (bs, 1H, 3β-H), 4.07 (m, 1H, 20-H), 4.82 (dd, J=1.23 Hz, 2H, 23-H), 5.20 (q, J=6.6 Hz, 1H, 21-H).

¹³C NMR δ: 11.18, 12.42, 20.64, 24.43, 25.29, 28.54, 29.03, 32.06, 32.18, 35.39, 35.88, 36.13, 39.15, 39.85, 42.74, 54.41, 56.03, 56.75, 66.59, 72.56, 77.16, 94.89, 207.05. IR(cm⁻¹): 1995 (C=C=CH₂), 1255 (C—O)

Elemental analysis $C_{23}H_{36}O_2$% Calc C:80.18, H:10.53, Found C:79.93, H:10.67.

More polar diastereomer
m.p.: 174–177° C.

¹H NMR δ: 0.66 (s, 3H, 18-CH₃), 0.77 (s, 3H, 19-CH₃), 0.79–1.91 (m, 23H), 4.03 (bs, 2H, 3β-H, 20-H), 4.79 (dd, J=0.90 Hz, 2H, 23-H), 5.20 (q, J=6.4 Hz, 1H, 21-H).

¹³C NMR δ: 11.17, 12.98, 20.48, 24.11, 25.95, 28.53, 29.02, 32.00, 32.19, 35.14, 35.88, 36.21, 38.92, 39.14, 41.96, 54.42, 56.17, 56.91, 66.57, 72.92, 77.19, 94.76, 207.60. IR(cm⁻¹): 1995 (C=C=CH₂), 1255 (C—O)

Elemental analysis $C_{23}H_{36}O_2$% Calc. C:80.18, H:10.53, Found C:79.97, H:10.63.

Example 15

3-Trimethylsilyl 1-methoxy-1-[3α-(t-butyldiphenyl-silyloxy)-5α-androstan-17β-yl]-2-propyne To a solution of trimethylsilylacetylene (0.066 mL, 0.48 mmol) in anhydrous THF (2 mL) at 0° C. was added a solution of n-BuLi (0.3 mL, 0.48 mmol) 1.6 M in hexanes and the resulting mixture was stirred for 2 h. Subsequently, the mixture was cooled to −78° C. and a solution of 3α-(t-butyldiphenylsilyloxy)-5α-androstan-17β-carboxaldehyde (90 mg, 0.16 mmol) in THF (2 mL) was added and the mixture was stirred at this temperature for 3 h after which iodomethane (0.1 mL, 1.6 mmol) was added and the resulting mixture was stirred at RT for 24 h. Quenching of the reaction by the addition of NH₄Cl was followed by extraction with ethyl acetate. The organic layer was washed with water, brine, dried with (Na₂SO₄) and the solvent was evaporated in vacuo. Subsequent purification of the residue with flash column chromatography using petroleum ether/ethyl acetate 95/5 as eluent afforded the desired compound named above. Separation of the two epimers was accomplished with preparative thin layer chromatography using petroleum etherlacetone 98/2 as eluent.

Yield: 80 mg, 73%
Less polar diastereomer
m.p.: 58–61° C.

¹H NMR δ: 0.16 (s, 9H, Si(CH₃)₃), 0.66 (s, 3H, 18-CH₃), 0.71 (s, 3H, 19-CH₃), 0.85–2.04 (m, 23H), 3.36 (s, 3H, OCH₃), 3.83 (d, J=9.81 Hz, 1H, 20-H), 4.00 (bs, 1H, 3β-H), 7.35–7.40 (m, 6H, aromatic), 7.64–7.66 (m, 4H, aromatic).

¹³C NMR δ: −0.06, 11.36, 12.39, 19.35, 20.62, 24.31, 25.46, 27.06, 28.60, 29.34, 29.67, 32.27, 32.65, 35.53, 36.07, 36.20, 39.35, 42.61, 53.38, 54.22, 54.61, 55.88, 68.10, 73.98, 75.22, 90.06, 127.40, 129.35, 134.83, 135.77.

Elemental analysis $C_{42}H_{61}O_2Si_2$% Calc C:77.13, H:9.41, Found C:76.73, H:9.38.

More polar diastereomer m.p.: 54–56° C.

$^1$H NMR δ: 0.17 (s, 9H, Si(CH$_3$)$_3$), 0.69 (s, 3H, 18-CH$_3$), 0.72 (s, 3H, 19-CH$_3$), 0.85–2.28 (m, 23H), 3.37 (s, 3H, OCH$_3$), 3.69 (d, J=9.80 Hz, 1H, 20-H), 4.00 (bs, 1H, 3β-H), 7.34–7.40 (m, 6H, aromatic), 7.64–7.65 (m, 4H, aromatic).

$^{13}$C NMR δ: −0.15, 11.39, 12.75, 19.35, 20.52, 26.85, 27.04, 28.57, 29.34, 30.56, 31.93, 32.27, 32.73, 35.26, 36.04, 36.18, 39.38, 41.77, 54.45, 54.64, 55.78, 56.13, 65.54, 68.09, 73.81, 91.23, 127.34, 129.35, 134.90, 135.77.

Elemental analysis C$_{42}$H$_{61}$O$_2$Si$_2$% Calc C:77.13, H:9.41, Found C:76.82, H:9.24.

Example 16

17β-(1-methoxy-2-propynyl)-5α-androstan-3α-ol

The deprotection of 3α-OH and the removal of the trimethylsilyl group of the diastereomers of Example 15 was accomplished in one step using (n-Bu)$_4$N$^+$F$^−$ 1M solution in THF (1.9 mL, 1.9 mmol) to a solution of the above compound (50 mg, 0.076 mmol) in THF (3 mL). The solution was stirred at RT for 24 h and was worked up as in Example 7 to afford after purification by flash column chromatography using petroleum etherfacetone 82/18 as elution solvent the compound of the Example 16.

Yield: 21 mg, 80%

Less polar diastereomer m.p.: 171–173° C.

$^1$H NMR δ: 0.66 (s, 3H, 18CH$_3$), 0.77 (s, 3H, 19-CH$_3$), 0.86–2.34 (m, 23H), 2.37 (d, J=1.7 Hz, 1H), 3.36 (s, 3H, OCH$_3$), 3.82 (dd, J=10.37 Hz, 1H. 20-H), 4.02 (bs, 1H, 3β-H).

$^{13}$C NMR β: 11.20, 12.36, 20.55, 24.27, 25.36, 28.53, 29.03, 32.04, 35.43, 35.88, 36.12, 39.13, 39.32, 42.58, 54.09, 54.41, 55.90, 56.13, 66.58, 73.34, 73.46, 82.89. Elemental analysis C$_{23}$H$_{35}$O$_2$% Calc. C:80.4, H:10.28, Found C:80.02, H:10.22.

More polar diastereomer m.p.: 161–163° C.

$^1$H NMR δ: 0.69 (s, 3H, 18-CH$_3$), 0.77 (s, 3H, 19-CH$_3$), 0.79–2.24 (m, 23H), 2.44 (d, J=1.83 Hz, 1H), 3.37 (s, 3H, OCH$_3$), 3.70 (dd, J=9.8 Hz, 1H, 20-H), 4.03 (bs, 1H, 3β-H).

$^{13}$C NMR δ: 10.74, 11.94, 20.44, 23.89, 26.62, 28.54, 29.02, 32.03, 32.16, 35.17, 35.89, 36.11, 38.63, 39.14, 41.74, 54.28, 54.37, 55.90, 56.13, 66.58, 73.11, 74.59, 82.95. Elemental analysis C$_{23}$H$_{35}$O$_2$% Calc C:80.4, H:10.28, Found C:80.15, H:10.01.

Example 17

1-[3α-(t-butyldiphenysilyloxy)-5α-androstan-17β-yl]-2-propyn-1-ol

A solution of (n-Bu)$_4$N$^+$F$^−$ 1M in THF (0.72 mL, 0.72 mmol) was added to a solution of 3-trimethylsilyl-1-[3α-(t-butyidiphenylsilyloxy)-5α-androstan-17β-yl]-2-propyn-1-ol (310 mg, 0.48 mmol) in THF (10 mL) and the resulting mixture was stirred at RT for 30 min. The reaction mixture was worked up as in Example 7 to afford after purification by flash column chromatography using petroleum ether/acetone 82/18 as elution solvent the compound named above.

Yield: 230 mg, 84%.

m.p.: 178–180° C.

$^1$H NMR δ: 0.70, 0.72, 0.73 (s, 9H, 18,19-CH$_3$ of diastereomers), 0.78–2.23 (m, 46H), 2.42 (d, J=1.8 Hz, 1H, acetylenic H), 2.50 (d, J=2.04 Hz, 1H, acetylenic H), 4.00 (bs, 2H, 3β-H of diastereomers), 4.20–4.26 (m, 1H, 20-H), 4.28–4.31 (m, 1H, 20-H), 7.33–7.43 (m, 12H), 7.64–7.72 (m, 8H, aromatic).

$^{13}$C NMR δ: 11.39, 11.45, 12.26, 12.33 19.35, 20.62, 24.32, 25.35, 27.05, 28.53, 29.31, 32.31, 32.65, 35.45, 36.05, 36.15, 39.35, 39.60, 42.57, 54.54, 55.97, 56.65, 64.74, 68.06, 72.52, 85.37, 127.42, 129.37, 134.77, 135.77.

Elemental analysis C$_{38}$H$_{52}$O$_2$Si % Calc. C:80.23, H:9.21, Found. C:80.53, H:9.58.

Example 18

1-{3α-(t-butyldiphenysilyloxy)-5α-androstan-17β-yl-[3-(4-methoxyphenyl)-2-propynyl]}-1-ol A solution of 1-[3α-(t-butyldiphenysilyloxy)-5α-androstan-17β-yl]-2-propyn-1-ol (100 mg, 0.176 mL) in pyrrolidine (2.5 mL) was added to a solution of 4-iodoanisole (82.38 mg, 0.35 mmol), CuI (19 mg, 0.1 mmol) and tetrakis (triphenylphosphine) palladium (0) (58 mg, 0.05 mmol) in pyrrolidine (1.5 mL). The resulting mixture was stirred for 24 h at RT. Quenching of the reaction by the addition of NH$_4$Cl was followed by extraction with ethyl acetate. The organic layer was washed with water, brine, dried with (Na$_2$SO$_4$) and the solvent was evaporated in vacuo. Subsequent purification of the residue with flash column chromatography using petroleum ether/acetone 80/20 as eluent afforded the desired compound named above.

Yield: 84%

Less polar diastereomer (67 mg)

m.p.: 63–65° C.

$^1$H NMR δ: 0.72 (s, 3H, 19-CH$_3$), 0.77 (s, 3H, 18-CH$_3$), 1.06 (s, 9H, C(CH$_3$)$_3$), 1.12–2.16 (m, 23H), 3.79 (s, 3H, OCH$_3$), 4.00 (bs, 1H, 3β-H), 4.46–4.51 (m, 1H, 20-H), 6.81 (d, J=9.0 Hz, 2H), 7.32–7.40 (m, 8H), 7.64–7.71 (m, 4H).

$^{13}$C NMR δ: 11.42, 12.42, 19.35, 20.65, 24.36, 25.07, 27.06, 28.56, 30.06, 32.32, 32.67, 35.48, 35.72, 36.07, 39.37, 39.63, 42.60, 54.56, 55.27, 56.03, 57.11, 65.03, 68.07, 85.34, 89.20, 113.85, 116.30, 127.42, 129.37, 133.04, 134.78, 135.78, 159.61.

Elemental analysis C$_{45}$H$_{57}$O$_3$Si % Calc. C:80.19, H:8.53, Found C:79.90, H:8.49.

More polar diastereomer (39 mg)

m.p.: 50–53° C.

$^1$H NMR δ: 0.71 (s, 3H, 19-CH$_3$), 0.74 (s, 3H, 18-CH$_3$), 1.06 (s, 9H, C(CH$_3$)$_3$), 1.12–2.29 (m, 23H), 3.80 (s, 3H, OCH$_3$), 4.00 (bs, 1H, 3βH), 4.33–4.38 (m, 1H, 20-H), 6.83 (d, J=8.72 Hz, 2H), 7.32–7.42 (m, 8H), 7.63–7.71 (m, 4H).

$^{13}$C NMR δ: 11.42, 12.82, 19.35, 20.63, 24.05, 26.63, 27.05, 28.56, 29.34, 32.36, 32.71, 35.23, 36.04, 36.16, 38.62, 39.39, 42.09, 54.64, 55.28, 56.19, 57.11, 65.08, 68.09, 85.44, 89.19, 113.93, 115.01, 127.33, 129.37, 132.96, 134.78, 135.77, 159.62. Elemental analysis C$_{45}$H$_{57}$O$_3$Si % Calc. C:80. 19, H:8.53, Found C:79.82, H:8.51.

Example 19

17β-[1-hydroxy-3-(4-methoxyphenyl)-2-propynyl]-5α-androstan-3α-ol

Removal of the protecting group of each of the two diastereomers mentioned in Example 18 was accomplished as in Example 7 to afford after flash column purification using dichloromethane/ethyl acetate (90/10) as elution solvent the compound named above.

Yield: 77%

Less polar diastereomer m.p.: 185–188° C.

¹H NMR δ: 0.76 (s, 3H, 19-CH₃), 0.78 (s, 3H, 18-CH₃), 0.81–2.08 (m, 23H), 3.79 (s, 1H, aromatic-OCH₃), 4.03 (bs, 1H, 3β-H), 4.45–4.49 (m, 1H, 20-H), 6.80 (d, J=8.8 Hz, 2H, aromatic), 7.32 (d, J=8.8 Hz, 2H, aromatic).

¹³C NMR δ: 11.19, 12.38, 20.58, 24.30, 25.45, 28.52, 29.02, 32.02, 32.16, 35.40, 35.87, 36.14, 39.14, 39.61, 42.56, 54.42, 55.26, 56.07, 57.07, 65.28, 66.60, 84.40, 89.22, 113.86, 114.99, 133.03, 159.52.

Elemental analysis $C_{29}H_{39}O_3$% Calc. C:79.95, H:9.03, Found C:79.59, H:8.97.

More polar diastereomer m.p.: 159–161° C.

¹H NMR δ: 0.73 (s, 3H, 18-CH₃), 0.76 (s, 3H, 19-CH₃), 0.85–2.25 (m, 23H), 3.79 (s, 1H, aromatic-OCH₃), 4.03 (bs, 1H, 3β-H), 4.33–4.36 (m, 1H, 20-H), 6.81 (d, J=8.8 Hz, 2H, aromatic), 7.33–7.36 (d, J=8.8 Hz, 2H, aromatic).

¹³C NMR δ: 11.20, 12.78, 20.56, 24.02, 26.62, 28.53, 29.02, 32.03, 32.19, 35.16, 35.87, 36.13, 38.57, 39.15, 42.65, 54.39, 55.27, 56.17, 57.03, 65.03, 66.58, 85.41, 89.17, 113.92, 114.98, 132.94, 159.61.

Elemental analysis $C_{29}H_{39}O_3$% Calc. C:79.95, H:9.03, Found C:79.65, H:8.69.

Example 20

3α-Azido-5α-pregnan-20-one

A solution of 3β-hydroxy-5α-pregnan-20-one (60 mg, 0.19 mmol) in THF (2 mL) was treated with triphenylphosphine (100 mg, 0.38 mmol) and diethyl azo-dicarboxylate (0.03 mL, 0.19 mmol). To the resulting solution was added dropwise diphenylphosphoryl azide (0.04 mL, 0.19 mmol) and the mixture was stirred at RT for 24 h. Evaporation of the solvent in vacuo and purification of the residue using flash column chromatography using petroleum ether/ethyl acetate 90/10 as elution solvent afforded the compound named above.

Yield: 41.5 mg, 64% m.p.: 159–162° C.

¹H NMR (CDCl₃) δ: 0.58 (s, 3H, 18-CH₃), 0.77 (s, 3H, 19-CH₃), 0.80–2.02 (m, 22H), 2.09 (s, 3H, COCH₃), 2.51 (t, J=8.8 Hz, 1H, 17α-H), 3.86 (bs, 1H, 3β-H).

¹³C NMR (CDCl₃) δ: 11.52, 13.41, 20.71, 22.72, 24.31, 25.55, 28.12, 31.51, 31.76, 32.45, 32.81, 35.37, 35.86, 38.97, 39.96, 44.18, 53.94, 56.64, 58.07, 63.74, 209.63. Elemental analysis $C_{21}H_{33}ON_3$% Calc. C:73.41, H:9.69, Found. C:73.02, H:9.35.

Example 21

3α-Azido-21-bromo-5α-pregnan-20-one

To a solution of 3α-azido-5α-pregnan-20-one (51.5 mg, 0.15 mmol) in absolute ethanol (3 mL) and chloroform (3 mL) was added pyridinium bromide perbromide (143 mg, 0.44 mmol) and the resulting mixture was heated at 50° C. for 45 min. Subsequently the mixture was diluted with dichloromethane and the organic layer was washed with water, brine and dried (Na₂SO₄). Evaporation of the solvent in vacuo and purification of the residue using flash column chromatography and petroleum ether/ethyl acetate 90/10 as elution solvent afforded the compound named above.

Yield: 60 mg, 95%.

m.p.: 108–110° C.

¹H NMR (CDCl₃) δ: 0.61 (s, 3H, 18-CH₃), 0.77 (s, 3H, 19-CH₃), 0.78–2.64 (m, 22H), 2.80 (t, J=8.8 Hz, 1H, 17α-H), 3.87 (bs, 1H, 3/3-H), 3.89 (s, 2H, CH₂Br).

¹³C NMR (CDCl₃) δ: 13.74, 14.82, 20.76, 23.71, 24.46, 25.60, 28.15, 31.79, 32.49, 32.86, 35.48, 35.93, 38.89, 40.00, 45.06, 53.18, 53.92, 56.64, 58.11, 60.53, 202.12. Elemental analysis $C_{21}H_{32}ON_3Br$% Calc. C:59.83, H:7.66, Found C:59.43, H:7.58.

Example 22

3α,21-di-azido-5α-pregnan-20-one

A solution of 3α-azido-21-bromo-5α-pregnan-20-one (35 mg, 0.083 mmol) in DMSO (3 mL) was treated with sodium azide (33 mg, 0.5 mmol) and the resulting mixture was stirred at RT for 24 h. Addition of water and ethyl acetate and extraction of the organic layer with water, brine, drying (Na₂SO₄) and evaporation of the solvent in vacuo afforded after purification of the residue using flash colunm chromatography with dichloromethane/ethyl acetate 90/10 as elution solvent the compound named above.

Yield: 17.65 mg, 55%.

m.p.: 133–135° C.

¹H NMR (CDCl₃) δ: 0.64 (s, 3H, 18-CH₃), 0.78 (s, 3H, 19-CH₃), 0.82–2.37 (m, 22H), 2.49 (t, J=9 Hz, 1H, 17α-H), 3.85 (s, 2H, CH₂N₃), 3.86 (bs, 1H, 3βH).

¹³C NMR (CDCl₃) δ: 11.55, 13.70, 20.70, 23.01, 24.42, 25.56, 28.09, 31.76, 32.46, 32.83, 35.40, 35.89, 38.92, 39.96, 44.96, 53.89, 56.74, 58.07, 58.43, 60.63, 204.88. Elemental analysis $C_{21}H_{32}ON_6$% Calc. C:65.58, H:8.39, Found C:65.21, H:8.89.

Biological Evaluation

Recently, the existence of an additional novel modulatory site on gamma-amino butyric acid $GABA_A$ receptor complex for specific steroid metabolites, such as 5α-pregnan-3α-ol-20-one (5PG), a reduced progesterone metabolite, was demonstrated pharmacologically in brain homogenates and in expressed recombinant receptors. This steroid binding site is functionally coupled to other modulatory sites on the $GABA_A$ receptor complex (Lan, N. C., Chen, J-S., Johnson, D., Gee K. W. Differential effects of 4'-chlordiazepam on expressed human $GABA_A$ receptors. *J. of Neurochem.* 1995, 684–88). According to Gee et al. (Gee K. W., Bolger, M. B., Wieland, S., Belleli, D., and Chen, J. S. Pharmacology of a $GABA_A$ receptor coupled steroid recognition site. *Synaptic Transmission* 1992, 111–17) and Wilson (Wilson, M. A., Influences of gender, gonadectomy, and estrous cycle on GABA/BZ receptors and benzodiazepine responses in rats. *Brain Res. Bull.* 1992, 165–72) benzodiazepines and steroid hormone derivatives can potentiate the inhibitory actions of GABA through interactions with the $GABA_A$/BZ/chloride channel complex. Binding of these steroid analogs to their respective site on the $GABA_A$/BZ/chloride channel complex causes a modification of all other receptor sites within the complex, including the benzodiazepine site. Therefore, neurosteroids allosterically enhance the binding of a benzodiazepine to the benzodiazepine receptor site. The ability of the new compounds to enhance the binding of [³H]-Flunitrazepam to the benzodiazepine site in rat brain GBR enriched synaptosomal preparation was initially evaluated as set forth below.

A 10 mM solution in DMSO of the compouds under investigation is diluted to 2 mM with 1% BSA in TME buffer, followed by a tenfold dilution with TME buffer. Subsequent dilutions were made with 0.1% BSA in TME buffer. Serial dilutions of the compounds under investigation were incubated with 1 nM [³H]-Flunitrazepam solution and 40 μg of synaptosomal membrane from rat brain at 30° C.

for 30 min. The assays were immediately filtered on Whatman GF/C filters using a Brandell M-24 cell harvester. Following four washes with wash buffer (0.4 M Tris-base, 60 nM $MgCl_2$, pH=7.4), the filters were collected in 5 mL scintillation fluid, and counted in a Beckman liquid scintillation counter LS1801 to determine the bound ligand. Nonspecific binding was determined using 50 μM diazepam. Specific binding was normalized to the control (with no test compound) and Log dose-specific binding curves were fitted by a logistic non-linear four parameter equation.

Table 1 provides $EC_{50}$ and maximum stimulation measurements for compounds disclosed and claimed herein. $EC_{50}$ is an indication of a compound's in vitro potency and maximum stimulation is an indication of a compound's in vitro efficacy. The results of the biological evaluation of compounds of the present invention are shown in Table 1.

TABLE 1

| COMPOUND | $EC_{50}$ (nM) | Maximum stimulation % |
| --- | --- | --- |
| 17β-[2-(4-tolyl)ethynyl]-5α-androstane-3α-ol | 2376 | 52.6 |
| 17β-(2-methoxycarbonylethynyl)-5α-androstane-3α-ol | 514.8 | 55.6 |
| 17β-(2-bromoethynyl)-5α-androstane-3α-ol | 326.4 | 72.7 |
| 17β-(3-hydroxy-1-butynyl)-5α-androstane-3α-ol | inactive | |
| 17β-(3-oxo-1-butynyl)-5α-androstan-3α-ol | inactive | |
| 3α,21-di-azido-5α-pregnan-20-one | 314.1 | 16.4 |
| 17β-[1-hydroxy-3-(4-methoxyphenyl)-2-propynyl]-5α-androstan-3α-ol (more polar C-20 epimer) | 36.31 | 23.3 |
| 17β-(1-hydroxy-2,3-butadienyl)-5α-androstane-3ol (mixture of C-20 epimers) | 5.9 | 45.8 |
| 17β-(1-methoxy-2-propynyl)-5α-androstan-3α-ol (mixture of C-20 epimers) | 4.48 | 18.1 |
| 17β-(1-hydroxy-2-propynyl)-5α-androstan-3-ol (less polar C-20 epimer) | inactive | |
| 3α-azido-5α-pregnan-20-one | inactive | |
| 3α-hydroxy-5α-pregnan-20-one (control) | 212 | 36 |

The invention claimed is:

1. A compound represented by Formula (I):

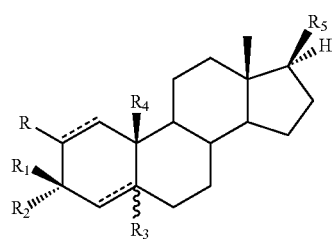

(I)

including pharmaceutically acceptable esters, salts and acid addition salts thereof, wherein:

R is one of hydrogen, amino, thio, sulfinyl, sulfonyl, sulfonamido, halogen, alkoxy, alkyl, alkenyl, or alkynyl and all R groups can be optionally substituted;

$R_1$ is one of hydrogen, alkyl, alkenyl, arylkynyl, alkoxyalkyl, aminoalkyl, cyano, cyanoalkyl, thiocyanoalkyl, isothiocyano, azidoalkyl, arylalkyl, arylalkenyl, aryl, arylkylalkynyl, alkanoyloxyalkynyl, heteroaryloxyalkynyl, oxoalkynyl or a ketal thereof, cyanoalkynyl, heteroarylalkynyl, hydroxyalkynyl, alkoxyalkynyl, aminoalkynyl, acylaminoalkynyl, mercaptoalkynyl, hydroxyalkynyl dioic acid hemi-ester or a salt thereof, or alkynyloxyalkynyl and all $R_1$ groups can be optionally substituted;

$R_2$ is one of hydroxyl, alkoxy, alkanoyloxy, aminocarbonyloxy, alkoxycarbonyloxy; azido, or NCS;

$R_3$ is hydrogen, or when a double bond is present between C4 and C5 of the steroid ring system, then $R_3$ is not present;

$R_4$ is one of hydrogen or lower alkyl, $R_5$ is one of —CH($OR_6$)$R_7$, —C≡C-aryl, —C≡C—CH($OR_6$)$R_8$, or —C≡C—C(O)$R_8$;

$R_6$ is independently H, optionally substituted $C_{1-10}$alkyl, optionally substituted $C_{2-10}$alkenyl, optionally substituted $C_{2-10}$alkynyl, optionally substituted aryl, optionally substituted arylkyl, optionally substituted C(O)—$C_{1-10}$alkyl, optionally substituted C(O)—$C_{2-10}$alkenyl, optionally substituted C(O)—$C_{2-10}$alkynyl $R_7$ is independently allene, optionally substituted alkynyl, optionally substituted arylkylalkynyl, optionally substituted alkanoyloxyalkynyl, optionally substituted heteroaryloxyalkynyl, oxoalkynyl or a ketal thereof, cyanoalkynyl, hydroxyalkynyl, alkoxyalkynyl, aminoalkynyl, acylaminoalkynyl, mercaptoalkynyl, hydroxyalkynyl dioic acid hemi-ester or a salt thereof, or alkynyloxyalkynyl;

$R_8$ is independently H, $C_{1-10}$alkyl, $C_{2-10}$alkenyl, $C_{2-10}$alkynyl, arylalkyl, aryl, all of which may be optionally substituted; and the dotted lines indicate that a single or double bond may be present.

2. A compound represented by Formula (I):

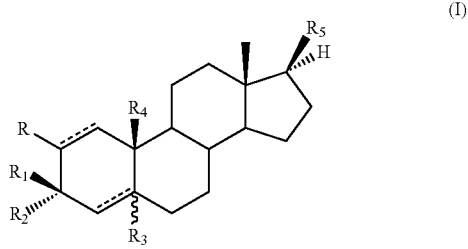

(I)

including pharmaceutically acceptable esters, salts and acid addition salts thereof, wherein:

R is one of hydrogen, amino, thio, sulfinyl, sulfonyl, sulfonamido, halogen, alkoxy, alkyl, alkenyl, or alkynyl and all R groups can be optionally substituted;

$R_1$ is one of alkyl, alkenyl, arylkynyl, alkoxyalkyl, aminoalkyl, cyano, cyanoalkyl, thiocyanoalkyl, isothiocyano, azidoalkyl, arylalkyl, arylalkenyl, aryl, arylkylalkynyl, alkanoyloxyalkynyl, heteroaryloxyalkynyl, oxoalkynyl or a ketal thereof, cyanoalkynyl, heteroarylalkynyl, hydroxyalkynyl, alkoxyalkynyl, aminoalkynyl, acylaminoalkynyl, mercaptoalkynyl, hydroxyalkynyl dioic acid hemi-ester or a salt thereof, or alkynyloxyalkynyl and all $R_1$ groups can be optionally substituted;

$R_2$ is one of hydroxyl, alkoxy, alkanoyloxy, aminocarbonyloxy or alkoxycarbonyloxy; azido, or NCS;

$R_3$ is hydrogen, or when a double bond is present between C4 and C5 of the steroid ring system, then $R_3$ is not present;

$R_4$ is one of hydrogen or lower alkyl, $R_5$ is —CH(X)—$R_6$; and

X is one of $N_3$, CN, or NCS, $R_6$ is independently H, optionally substituted $C_{1-10}$alkyl, optionally substituted $C_{2-10}$alkenyl, optionally substituted $C_{2-10}$alkynyl, optionally substituted aryl, optionally substituted arylkyl, optionally substituted C(O)—$C_{1-10}$alkyl, optionally substituted C(O)—$C_{2-10}$alkenyl, optionally substituted C(O)—$C_{2-10}$alkynyl; and the dotted lines indicate that a single or double bond may be present.

3. A compound represented by Formula (I):

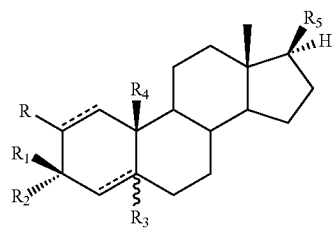

(I)

including pharmaceutically acceptable esters, salts and acid addition salts thereof, wherein:
R is one of hydrogen, amino, thio, sulfinyl, sulfonyl, sulfonamido, halogen, alkoxy, alkyl, alkenyl, or alkynyl and all R groups can be optionally substituted;
$R_1$ is one of hydrogen, alkyl, alkenyl, arylkynyl, alkoxyalkyl, aminoalkyl, cyano, cyanoalkyl, thiocyanoalkyl, isothiocyano, azidoalkyl, arylalkyl, arylalkenyl, aryl, arylkylalkynyl, alkanoyloxyalkynyl, heteroaryloxyalkynyl, oxoalkynyl or a ketal thereof, cyanoalkynyl, heteroarylalkynyl, hydroxyalkynyl, alkoxyalkynyl, aminoalkynyl, acylaminoalkynyl, mercaptoalkynyl, hydroxyalkynyl dioic acid hemi-ester or a salt thereof, or alkynyloxyalkynyl and all $R_1$ groups can be optionally substituted;
$R_2$ is $N_3$;
$R_3$ is hydrogen, or when a double bond is present between C4 and C5 of the steroid ring system, then $R_3$ is not present;
$R_4$ is one of hydrogen or lower alkyl,
$R_5$ is one of —C(O)CH$_2$N$_3$, —C(O)CH$_2$Br, or —C(O)CH$_3$; and
the dotted lines indicate that a single or double bond may be present.

4. A compound selected from one of the following, including pharmaceutically acceptable esters, salts and acid addition salts thereof:
17β-[2-(4-tolyl)ethynyl]-5α-androstane-3α-ol;
17β-(2-methoxycarbonylethynyl)-5α-androstane-3β-ol;
17β-(2-bromoethynyl)-5α-androstane-3α-ol;
17β-(3-hydroxy-1-butynyl)-5α-androstane-3α-ol;
17β-(3-oxo-1-butynyl)-5α-androstan-3α-ol;
17β-[1-hydroxy-3-(4-methoxyphenyl)-2-propynyl]-5α-androstan-3α-ol;
17β-(1-hydroxy-2,3-butadienyl)-5α-androstane-3-ol;
17β-(1-methoxy-2-propynyl)-5α-androstan-3a-ol;
17β-(1-hydroxy-2-propynyl)-5α-androstan-3-ol;
3α-Azido-5α-pregnan-20-one;
3α-Azido-21-bromo-5α-pregnan-20-one; or
3α,21-di-azido-5α-pregnan-20-one.

5. A method of inducing anesthesia; treating stress, treating anxiety, treating pre-menstrual syndrome, treating post-natal depression, and treating seizures; ameliorating attacks of anxiety, ameliorating muscle tension, or ameliorating depression common with patients suffering from central nervous system abnormalities, comprising
administering to a patient a compound represented by Formula (I):

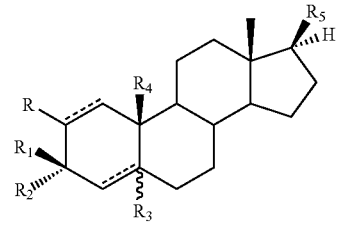

(I)

including pharmaceutically acceptable esters, salts and acid addition salts thereof, wherein:
R is one of hydrogen, amino, thio, sulfinyl, sulfonyl, sulfonamido, halogen, alkoxy, alkyl, alkenyl, or alkynyl and all R groups can be optionally substituted;
$R_1$ is one of alkyl, alkenyl, arylkynyl, alkoxyalkyl, aminoalkyl, cyano, cyanoalkyl, thiocyanoalkyl, isothiocyano, azidoalkyl, arylalkyl, arylalkenyl, aryl, arylkylalkynyl, alkanoyloxyalkynyl, heteroaryloxyalkynyl, oxoalkynyl or a ketal thereof, cyanoalkynyl, heteroarylalkynyl, hydroxyalkynyl, alkoxyalkynyl, aminoalkynyl, acylaminoalkynyl, mercaptoalkynyl, hydroxyalkynyl dioic acid hemi-ester or a salt thereof, or alkynyloxyalkynyl and all $R_1$ groups can be optionally substituted;
$R_2$ is one of hydroxyl, alkoxy, alkanoyloxy, aminocarbonyloxy, alkoxycarbonyloxy; azido, or NCS;
$R_3$ is hydrogen, or when a double bond is present between C4 and C5 of the steroid ring system, then $R_3$ is not present;
$R_4$ is one of hydrogen or lower alkyl,
$R_5$ is one of —CH(OR$_6$)R$_7$, —C≡C-aryl, —C≡C—CH(OR$_6$)R$_8$, or —C≡C—C(O)R$_8$;
$R_6$ is independently H, optionally substituted $C_{1-10}$alkyl, optionally substituted $C_{2-10}$alkenyl, optionally substituted $C_{2-10}$alkynyl, optionally substituted aryl, optionally substituted arylkyl, optionally substituted C(O)—$C_{1-10}$alkyl, optionally substituted C(O)—$C_{2-10}$alkenyl, optionally substituted C(O)—$C_{2-10}$alkynyl
$R_7$ is independently allene, optionally substituted alkynyl, optionally substituted arylkylalkynyl, optionally substituted alkanoyloxyalkynyl, optionally substituted heteroaryloxyalkynyl, oxoalkynyl or a ketal thereof, cyanoalkynyl, hydroxyalkynyl, alkoxyalkynyl, aminoalkynyl, acylaminoalkynyl, mercaptoalkynyl, hydroxyalkynyl dioic acid hemi-ester or a salt thereof, or alkynyloxyalkynyl;
$R_8$ is independently H, $C_{1-10}$alkyl, $C_{2-10}$alkenyl, $C_{2-10}$alkynyl, arylalkyl, aryl, all of which may be optionally substituted; and
the dotted lines indicate that a single or double bond may be present; or
a compound represented by Formula (I) above, including pharmaceutically acceptable esters, salts and acid addition salts thereof, wherein:
R is one of hydrogen, amino, thio, sulfinyl, sulfonyl, sulfonamido, halogen, alkoxy, alkyl, alkenyl, or alkynyl and all R groups can be optionally substituted;

R₁ is one of alkyl, alkenyl, arylkynyl, alkoxyalkyl, aminoalkyl, cyano, cyanoalkyl, thiocyanoalkyl, isothiocyano, azidoalkyl, arylalkyl, arylalkenyl, aryl, arylkylalkynyl, alkanoyloxyalkynyl, heteroaryloxyalkynyl, oxoalkynyl or a ketal thereof, cyanoalkynyl, heteroarylalkynyl, hydroxyalkynyl, alkoxyalkynyl, aminoalkynyl, acylaminoalkynyl, mercaptoalkynyl, hydroxyalkynyl dioic acid hemi-ester or a salt thereof, or alkynyloxyalkynyl and all R₁ groups can be optionally substituted;

R₂ is one of hydroxyl, alkoxy, alkanoyloxy, aminocarbonyloxy, alkoxycarbonyloxy; azido, or NCS;

R₃ is hydrogen, or when a double bond is present between C4 and C5 of the steroid ring system, then R₃ is not present;

R₄ is one of hydrogen or lower alkyl,

R₅ is —CH(X)—R₆; and

X is one of N₃, CN, or NCS,

R₆ is independently H, optionally substituted $C_{1-10}$alkyl, optionally substituted $C_{2-10}$alkenyl, optionally substituted $C_{2-10}$alkynyl, optionally substituted aryl, optionally substituted arylkyl, optionally substituted C(O)—$C_{1-10}$alkyl, optionally substituted C(O)—$C_{2-10}$alkenyl, optionally substituted C(O)—$C_{2-10}$alkynyl;

and the dotted lines indicate that a single or double bond may be present; or a compound represented by Formula (I) above, including pharmaceutically acceptable esters, salts and acid addition salts thereof, wherein:

R is one of hydrogen, amino, thio, sulfinyl, sulfonyl, sulfonamido, halogen, alkoxy, alkyl, alkenyl, or alkynyl and all R groups can be optionally substituted;

R₁ is one of alkyl, alkenyl, arylkynyl, alkoxyalkyl, aminoalkyl, cyano, cyanoalkyl, thiocyanoalkyl, isothiocyano, azidoalkyl, arylalkyl, arylalkenyl, aryl, arylkylalkynyl, alkanoyloxyalkynyl, heteroaryloxyalkynyl, oxoalkynyl or a ketal thereof, cyanoalkynyl, heteroarylalkynyl, hydroxyalkynyl, alkoxyalkynyl, aminoalkynyl, acylaminoalkynyl, mercaptoalkynyl, hydroxyalkynyl dioic acid hemi-ester or a salt thereof, or alkynyloxyalkynyl and all R₁ groups can be optionally substituted;

R₂ is N₃;

R₃ is hydrogen, or when a double bond is present between C4 and C5 of the steroid ring system, then R₃ is not present;

R₄ is one of hydrogen or lower alkyl,

R₅ is one of —C(O)CH₂N₃, —C(O)CH₂Br, or —C(O)CH₃; and the dotted lines indicate that a single or double bond may be present; or a compound selected from one of the following, including pharmaceutically acceptable esters, salts and acid addition salts thereof:

17β-[2-(4-tolyl)ethynyl]-5α-androstane-3α-ol;
17β-(2-methoxycarbonylethynyl)-5α-androstane-3β-ol;
17β-(2-bromoethynyl)-5α-androstane-3α-ol;
17β-(3-hydroxy-1-butynyl)-5α-androstane-3α-ol;
17β-(3-oxo-1-butynyl)-5α-androstan-3α-ol;
17β-[1-hydroxy-3-(4-methoxyphenyl)-2-propynyl]-5α-androstan-3α-ol;
17β-(1-hydroxy-2,3-butadienyl)-5α-androstane-3-ol;
17β-(1-methoxy-2-propynyl)-5α-androstan-3a-ol;
17β-(1-methoxy-2-propynyl)-5α-androstan-3-ol;
3α-Azido-5α-pregnan-20-one;
3α-Azido-21-bromo-5α-pregnan-20-one; or 3α,21-di-azido-5α-pregnan-20-one.

6. The method of claim 5 comprising the step of stimulating the $GABA_A$ receptor.

7. The method of claim 6 wherein;

R is one of hydrogen, amino, thio, sulfinyl, sulfonyl, sulfonamido, halogen, alkoxy, alkyl, alkenyl, or alkynyl and all R groups can be optionally substituted;

R₁ is one of alkyl, alkenyl, arylkynyl, alkoxyalkyl, aminoalkyl, cyano, cyanoalkyl, thiocyanoalkyl, isothiocyano, azidoalkyl, arylalkyl, arylalkenyl, aryl, arylkylalkynyl, alkanoyloxyalkynyl, heteroaryloxyalkynyl, oxoalkynyl or a ketal thereof, cyanoalkynyl, heteroarylalkynyl, hydroxyalkynyl, alkoxyalkynyl, aminoalkynyl, acylaminoalkynyl, mercaptoalkynyl, hydroxyalkynyl dioic acid hemi-ester or a salt thereof, or alkynyloxyalkynyl and all R₁ groups can be optionally substituted;

R₂ is one of hydroxyl, alkoxy, alkanoyloxy, aminocarbonyloxy, alkoxycarbonyloxy; azido, or NCS;

R₃ is hydrogen, or when a double bond is present between C4 and C5 of the steroid ring system, then R₃ is not present;

R₄ is one of hydrogen or lower alkyl,

R₅ is one of —CH(OR₆)R₇, —C≡C-aryl, —C≡C—CH(OR₆)R₈, or —C≡C—C(O)R₈;

R₆ is independently H, optionally substituted $C_{1-10}$alkyl, optionally substituted $C_{2-10}$alkenyl, optionally substituted $C_{2-10}$alkynyl, optionally substituted aryl, optionally substituted arylkyl, optionally substituted C(O)—$C_{1-10}$alkyl, optionally substituted C(O)—$C_{2-10}$alkenyl, optionally substituted C(O)—$C_{2-10}$alkynyl R₇ is independently allene, optionally substituted alkynyl, optionally substituted arylkylalkynyl, optionally substituted alkanoyloxyalkynyl, optionally substituted heteroaryloxyalkynyl, oxoalkynyl or a ketal thereof, cyanoalkynyl, hydroxyalkynyl, alkoxyalkynyl, aminoalkynyl, acylaminoalkynyl, mercaptoalkynyl, hydroxyalkynyl dioic acid hemi-ester or a salt thereof, or alkynyloxyalkynyl;

R₈ is independently H, $C_{1-10}$alkyl, $C_{2-10}$alkenyl, $C_{2-10}$alkynyl, arylalkyl, or aryl, all of which may be optionally substituted; and the dotted lines indicate that a single or double bond may be present.

8. The method of claim 6 wherein;

R is one of hydrogen, amino, thio, sulfinyl, sulfonyl, sulfonamido, halogen, alkoxy, alkyl, alkenyl, or alkynyl and all R groups can be optionally substituted;

R₁ is one of alkyl, alkenyl, arylkynyl, alkoxyalkyl, aminoalkyl, cyano, cyanoalkyl, thiocyanoalkyl, isothiocyano, azidoalkyl, arylalkyl, arylalkenyl, aryl, arylkylalkynyl, alkanoyloxyalkynyl, heteroaryloxyalkynyl, oxoalkynyl or a ketal thereof, cyanoalkynyl, heteroarylalkynyl, hydroxyalkynyl, alkoxyalkynyl, aminoalkynyl, acylaminoalkynyl, mercaptoalkynyl, hydroxyalkynyl dioic acid hemi-ester or a salt thereof, or alkynyloxyalkynyl and all R₁ groups can be optionally substituted;

R₂ is one of hydroxyl, alkoxy, alkanoyloxy, aminocarbonyloxy, alkoxycarbonyloxy; azido, or NCS;

R₃ is hydrogen, or when a double bond is present between C4 and C5 of the steroid ring system, then R₃ is not present;

R₄ is one of hydrogen or lower alkyl,

R₅ is —CH(X)—R₆; and

X is one of N₃, CN, or NCS,

R$_6$ is independently H, optionally substituted C$_{1-10}$alkyl, optionally substituted C$_{2-10}$alkenyl, optionally substituted C$_{2-10}$alkynyl, optionally substituted aryl, optionally substituted arylkyl, optionally substituted C(O)—C$_{1-10}$alkyl, optionally substituted C(O)—C$_{2-10}$alkenyl, optionally substituted C(O)—C$_{2-10}$alkynyl;

and the dotted lines indicate that a single or double bond may be present.

9. The method of claim 6 wherein;
R is one of hydrogen, amino, thio, sulfinyl, sulfonyl, sulfonamido, halogen, alkoxy, alkyl, alkenyl, or alkynyl and all R groups can be optionally substituted;
R$_1$ is one of hydrogen, alkyl, alkenyl, arylkynyl, alkoxyalkyl, aminoalkyl, cyano, cyanoalkyl, thiocyanoalkyl, isothiocyano, azidoalkyl, arylalkyl, arylalkenyl, aryl, arylkylalkynyl, alkanoyloxyalkynyl, heteroaryloxyalkynyl, oxoalkynyl or a ketal thereof, cyanoalkynyl, heteroarylalkynyl, hydroxyalkynyl, alkoxyalkynyl, aminoalkynyl, acylaminoalkynyl, mercaptoalkynyl, hydroxyalkynyl dioic acid hemi-ester or a salt thereof, or alkynyloxyalkynyl and all R$_1$ groups can be optionally substituted;
R$_2$ is N$_3$;
R$_3$ is hydrogen, or when a double bond is present between C4 and C5 of the steroid ring system, then R$_3$ is not present;
R$_4$ is one of hydrogen or lower alkyl,
R$_5$ is one of —C(O)CH$_2$N$_3$, —C(O)CH$_2$Br, or —C(O)CH$_3$; and
the dotted lines indicate that a single or double bond may be present.

10. The method of claim 6 wherein; the compound is selected from:
17β-[2-(4-tolyl)ethynyl]-5α-androstane-3α-ol;
17β-(2-methoxycarbonylethynyl)-5α-androstane-3β-ol;
17β-(2-bromoethynyl)-5α-androstane-3α-ol;
17β-(3-hydroxy-1-butynyl)-5α-androstane-3α-ol;
17β-(3-oxo-1-butynyl)-5α-androstan-3α-ol;
17β-[1-hydroxy-3-(4-methoxyphenyl)-2-propynyl]-5α-androstan-3α-ol;
17β-(1-hydroxy-2,3-butadienyl)-5α-androstane-3-ol;
17β-(1-methoxy-2-propynyl)-5α-androstan-3a-ol;
17β-(1-hydroxy-2-propynyl)-5α-androstan-3-ol;
3α-Azido-5α-pregnane-20-one;
3α-Azido-21-bromo-5α-pregnan-20-one; or
3α,21-di-azido-5α-pregnan-20-one.

11. The method of claim 5 wherein;
R is one of hydrogen, amino, thio, sulfinyl, sulfonyl, sulfonamido, halogen, alkoxy, alkyl, alkenyl, or alkynyl and all R groups can be optionally substituted;
R$_1$ is one of alkyl, alkenyl, arylkynyl, alkoxyalkyl, aminoalkyl, cyano, cyanoalkyl, thiocyanoalkyl, isothiocyano, azidoalkyl, arylalkyl, arylalkenyl, aryl, arylkylalkynyl, alkanoyloxyalkynyl, heteroaryloxyalkynyl, oxoalkynyl or a ketal thereof, cyanoalkynyl, heteroarylalkynyl, hydroxyalkynyl, alkoxyalkynyl, aminoalkynyl, acylaminoalkynyl, mercaptoalkynyl, hydroxyalkynyl dioic acid hemi-ester or a salt thereof, or alkynyloxyalkynyl and all R$_1$ groups can be optionally substituted;
R$_2$ is one of hydroxyl, alkoxy, alkanoyloxy, aminocarbonyloxy, alkoxycarbonyloxy; azido, or NCS;
R$_3$ is hydrogen, or when a double bond is present between C4 and C5 of the steroid ring system, then R$_3$ is not present;
R$_4$ is one of hydrogen or lower alkyl,
R$_5$ is one of —CH(OR$_6$)R$_7$, —C≡C-aryl, —C≡C—CH(OR$_6$)R$_8$, or —C≡C—C(O)R$_8$;
R$_6$ is independently H, optionally substituted C$_{1-10}$alkyl, optionally substituted C$_{2-10}$alkenyl, optionally substituted C$_{2-10}$alkynyl, optionally substituted aryl, optionally substituted arylkyl, optionally substituted C(O)—C$_{1-10}$alkyl, optionally substituted C(O)—C$_{2-10}$alkenyl, optionally substituted C(O)—C$_{2-10}$alkynyl
R$_7$ is independently allene, optionally substituted alkynyl, optionally substituted arylkylalkynyl, optionally substituted alkanoyloxyalkynyl, optionally substituted heteroaryloxyalkynyl, oxoalkynyl or a ketal thereof, cyanoalkynyl, hydroxyalkynyl, alkoxyalkynyl, aminoalkynyl, acylaminoalkynyl, mercaptoalkynyl, hydroxyalkynyl dioic acid hemi-ester or a salt thereof, or alkynyloxyalkynyl;
R$_8$ is independently H, C$_{1-10}$alkyl, C$_{2-10}$alkenyl, C$_{2-10}$alkynyl, arylalkyl, or aryl, all of which may be optionally substituted; and
the dotted lines indicate that a single or double bond may be present.

12. The method of claim 5 wherein;
R is one of hydrogen, amino, thio, sulfinyl, sulfonyl, sulfonamido, halogen, alkoxy, alkyl, alkenyl, or alkynyl and all R groups can be optionally substituted;
R$_1$ is one of alkyl, alkenyl, arylkynyl, alkoxyalkyl, aminoalkyl, cyano, cyanoalkyl, thiocyanoalkyl, isothiocyano, azidoalkyl, arylalkyl, arylalkenyl, aryl, arylkylalkynyl, alkanoyloxyalkynyl, heteroaryloxyalkynyl, oxoalkynyl or a ketal thereof, cyanoalkynyl, heteroarylalkynyl, hydroxyalkynyl, alkoxyalkynyl, aminoalkynyl, acylaminoalkynyl, mercaptoalkynyl, hydroxyalkynyl dioic acid hemi-ester or a salt thereof, or alkynyloxyalkynyl and all R$_1$ groups can be optionally substituted;
R$_2$ is one of hydroxyl, alkoxy, alkanoyloxy, aminocarbonyloxy, alkoxycarbonyloxy; azido, or NCS;
R$_3$ is hydrogen, or when a double bond is present between C4 and C5 of the steroid ring system, then R$_3$ is not present;
R$_4$ is one of hydrogen or lower alkyl,
R$_5$ is —CH(X)—R$_6$; and
X is one of N$_3$, CN, or NCS,
R$_6$ is independently H, optionally substituted C$_{1-10}$alkyl, optionally substituted C$_{2-10}$alkenyl, optionally substituted C$_{2-10}$alkynyl, optionally substituted aryl, optionally substituted arylkyl, optionally substituted C(O)—C$_{1-10}$alkyl, optionally substituted C(O)—C$_{2-10}$alkenyl, optionally substituted C(O)—C$_{2-10}$alkynyl;
and the dotted lines indicate that a single or double bond may be present.

13. The method of claim 5 wherein;
R is one of hydrogen, amino, thio, sulfinyl, sulfonyl, sulfonamido, halogen, alkoxy, alkyl, alkenyl, or alkynyl and all R groups can be optionally substituted;
R$_1$ is one of hydrogen, alkyl, alkenyl, arylkynyl, alkoxyalkyl, aminoalkyl, cyano, cyanoalkyl, thiocyanoalkyl, isothiocyano, azidoalkyl, arylalkyl, arylalkenyl, aryl, arylkylalkynyl, alkanoyloxyalkynyl, heteroaryloxyalkynyl, oxoalkynyl or a ketal thereof, cyanoalkynyl, heteroarylalkynyl, hydroxyalkynyl, alkoxyalkynyl, aminoalkynyl, acylaminoalkynyl, mercaptoalkynyl, hydroxyalkynyl dioic acid hemi-ester or a salt thereof, or alkynyloxyalkynyl and all R$_1$ groups can be optionally substituted;

R₂ is N₃;

R₃ is hydrogen, or when a double bond is present between C4 and C5 of the steroid ring system, then R₃ is not present;

R₄ is one of hydrogen or lower alkyl,

R₅ is one of —C(O)CH₂N₃, —C(O)CH₂Br, or —C(O)CH₃; and the dotted lines indicate that a single or double bond may be present.

14. The method of claim 5 wherein; the compound is selected from:

17β-[2-(4-tolyl)ethynyl]-5α-androstane-3α-ol;
17β-(2-methoxycarbonylethynyl)-5α-androstane-3β-ol;
17β-(2-bromoethynyl)-5α-androstane-3α-ol;
17β-(3-hydroxy-1-butynyl)-5α-androstane-3α-ol;
17β-(3-oxo-1-butynyl)-5α-androstan-3α-ol;
17β-[1-hydroxy-3-(4-methoxyphenyl)-2-propynyl]-5α-androstan-3α-ol;
17β-(1-hydroxy-2,3-butadienyl)-5α-androstane-3-ol;
17β-(1-methoxy-2-propynyl)-5α-androstan-3a-ol;
17β-(1-hydroxy-2-propynyl)-5α-androstan-3-ol;
3α-Azido-5α-pregnan-20-one;
3α-Azido-21-bromo-5α-pregnan-20-one; or
3α,21-di-azido-5α-pregnan-20-one.

* * * * *

UNITED STATES PATENT AND TRADEMARK OFFICE
CERTIFICATE OF CORRECTION

PATENT NO. : 7,064,116 B2
APPLICATION NO. : 10/250334
DATED : June 20, 2006
INVENTOR(S) : Calogeropoulou et al.

It is certified that error appears in the above-identified patent and that said Letters Patent is hereby corrected as shown below:

Column 17:

Line 57, after "wherein" delete ":" and substitute --;--.

Column 18:

Line 46, after "wherein" delete ":" and substitute --;--.

Line 48, after "alkenyl," delete "or".

Column 19:

Line 24, after "wherein" delete ":" and substitute --;--.

Line 26, after "alkenyl," delete "or".

Line 51, delete "17β-(2-methoxycarbonylethynyl)-5α-androstane-3β-ol;" and substitute --17β-(2-methoxycarbonylethynyl)-5α-androstane-3α-ol;--.

Line 66, after "depression," delete "and".

Column 20:

Line 19, after "wherein" delete ":" and substitute --;--.

Line 23, before "alkyl" insert --hydrogen,--.

Column 21:

Line 30, after "wherein" delete ":" and substitute --;--.

Line 34, before "alkyl," insert --hydrogen,--.

Line 57, delete "17β-(2-methoxycarbonylethynyl)-5α-androstane-3β-ol;" and substitute --17β-(2-methoxycarbonylethynyl)-5α-androstane-3α-ol;--.

UNITED STATES PATENT AND TRADEMARK OFFICE
CERTIFICATE OF CORRECTION

PATENT NO. : 7,064,116 B2
APPLICATION NO. : 10/250334
DATED : June 20, 2006
INVENTOR(S) : Calogeropoulou et al.

It is certified that error appears in the above-identified patent and that said Letters Patent is hereby corrected as shown below:

Column 22:

Line 8, before "alkyl," insert --hydrogen,--.

Column 23:

Line 36, delete "17β-(2-methoxycarbonylethynyl)-5α-androstane-3β-ol;" and substitute --17β-(2-methoxycarbonylethynyl)-5α-androstane-3α-ol;--.

Line 52, before "alkyl," insert --hydrogen,--.

Column 25:

Line 13, delete "17β-(2-methoxycarbonylethynyl)-5α-androstane-3β-ol;" and substitute --17β-(2-methoxycarbonylethynyl)-5α-androstane-3α-ol;--..

Signed and Sealed this

Sixth Day of February, 2007

JON W. DUDAS
*Director of the United States Patent and Trademark Office*